United States Patent
Ding et al.

(10) Patent No.: US 6,280,389 B1
(45) Date of Patent: Aug. 28, 2001

(54) PATIENT IDENTIFICATION FOR THE PACING THERAPY USING LV-RV PRESSURE LOOP

(75) Inventors: Jiang Ding; Yinghong Yu, both of Maplewood; Julio Spinelli, Shoreview, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/439,228

(22) Filed: Nov. 12, 1999

(51) Int. Cl.[7] .................................................. A61B 5/021
(52) U.S. Cl. .............................................................. 600/485
(58) Field of Search ................................... 600/508, 485, 600/510, 526

(56) References Cited

U.S. PATENT DOCUMENTS

| | | | |
|---|---|---|---|
| 4,986,270 | 1/1991 | Cohen | 128/419 |
| 5,312,452 | 5/1994 | Salo | 607/17 |
| 5,334,222 | 8/1994 | Salo et al. | 607/17 |
| 5,466,245 | 11/1995 | Spinelli et al. | 607/17 |
| 5,487,752 | 1/1996 | Salo et al. | 607/17 |
| 5,540,727 | 7/1996 | Tockman et al. | 607/18 |
| 5,560,370 | 10/1996 | Verrier et al. | 128/705 |
| 5,800,471 | 9/1998 | Baumann | 607/25 |
| 5,976,082 | 11/1999 | Wong et al. | 600/300 |

OTHER PUBLICATIONS

Auricchio A., et al: "Effect of Pacing Chamber and Atrio–Ventricular Delay on Acute Systolic Function of Paced Heart Failure Patients in Path–CHF Study" Pace, vol. 21, No. 4, Part 02, Apr. 1, 1998, p. 827. XP–000778577.

Effect of Pacing Chamber and Atrioventricular Delay on Acute Systolic Function of Paced Patients with Congestive Heart Failure, Journal of the American Heart Association vol. 99, No. 23, Jun. 15, 1999.

Usefulness of Physiologic Dual–Chamber Pacing in Drug–Resistant Idiopathic Dilated Cardiomyopathy, The American Journal of Cardiology, vol. 66, Jul. 1, 1990.

*Primary Examiner*—Scott M. Getzow
(74) *Attorney, Agent, or Firm*—Nikolai, Mersereau & Dietz, P.A.

(57) ABSTRACT

A method and apparatus for determining whether a patient with congestive heart failure (CHF) will benefit from pacing therapy through the use of an implantable cardiac rhythm management device. A patient's right ventricular and left ventricular pressures are measured, and the patient's PP_Area is calculated for each normal heartbeat that occurs during the testing period. Depending upon the value of the patient's mean PP_Area, it can be determined whether the patient will or will not respond well acutely to pacing therapy. A mean PP_Area value of greater than or equal to a predetermined threshold, which is about 0.3, indicates that the patient is a responder to pacing therapy, while a value of less than the predetermined threshold of about 0.3 indicates that the patient is a non-responder.

17 Claims, 5 Drawing Sheets

PATIENT IDENTIFICATION FOR THE PACING THERAPY USING LV-RV PRESSURE LOOP

BACKGROUND OF THE INVENTION

I. Field of the Invention

This invention relates generally to implantable cardiac rhythm management devices used in medical treatment. More particularly, the present invention relates to a method and apparatus for determining whether a patient suffering from congestive heart failure (CHF) will benefit from pacing therapy through an implantable cardiac rhythm management device.

II. Description of the Prior Art

CHF is a disease that affects over two million Americans. Patients suffering from this disease typically manifest a degraded cardiac function, such as abnormally low cardiac output. The average life span of a patient diagnosed with CHF is just five years.

Implantable cardiac rhythm management devices, when they were first introduced, were simply used to deliver ventricular stimulating pulses to maintain a predetermined heart beat rate. More recently, as discussed in a paper entitled "Usefulness of physiologic dual-chamber pacing in drug-resistant idiopathic dilated cardiomyopathy" in the *American Journal of Cardiology* (Vol 66, Jul. 15, 1990, pp. 198–202), implantable cardiac rhythm management devices have been used to enhance the hemodynamic performance of the heart in patients suffering from CHF or other types of left ventricular dysfunction. It has been found that by pacing the left ventricle and appropriately setting the atrio-ventricular (AV) delay parameter of a pacemaker, the patient's cardiac output can be improved and optimized. The following patents include methods for optimizing the AV delay interval and/or pacing mode when treating CHF patients: the Salo U.S. Pat. No. 5,312,452; the Salo et al. U.S. Pat. Nos. 5,344,222 and 5,487,752; the Spinelli et al. U.S. Pat. No. 5,466,245; the Tockman U.S. Pat. No. 5,540,727; and the Baumann U.S. Pat. No. 5,800,471.

Pacing therapy has been found to have both positive and negative acute impact on CHF patients. In effect, some CHF patients respond well to the pacing therapy, and are called "responders", while others are negatively effected, and are called "non-responders". It is speculated that the different responses of CHF patients to pacing therapy are due to different patterns and/or degrees of conduction abnormalities in the hearts of the patients.

One study that has been published by *Circulation* (1999; 99:2993–3001) demonstrates the different responses of CHF patients to pacing therapy. Twenty-seven patients with New York Heart Association (NYHA) Class III/IV heart failure, and QRS duration greater than or equal to 120 msec, were enrolled in the "Pacing Therapies for Congestive Heart Failure" (PATH-CHF) study. Twenty-five of the patients were ultimately tested to see the effect of pacing chamber and AV delay on acute systolic function. These patients were paced at right (RV), left (LV) and both ventricles (BV) at one of five AV delays. Each combination of pacing chamber and AV delay was randomly repeated five times on each patient in a five-beat pacing/fifteen-beat no-pacing duty cycle.

The results of the test showed that pacing significantly increased both the LV pressure derivative maximum and pulse pressure for fifteen (15) of the patients (60%), increased only the LV pressure derivative maximum for five (5) of the patients (20%), and did not increase the LV pressure derivative maximum or pulse pressure for another five (5), which was 20%, of the patients. The group of five patients that did not have an increase in either their LV pressure derivative or pulse pressures were called "non-responders". The rest of the patients responded well to pacing and were considered to be "responders".

The PATH-CHF study revealed a trend with respect to the responders and non-responders. The study revealed that the responders had wider QRS complexes, as recorded on surface electrocardiograms (ECG), than the non-responders. Wider than normal QRS complexes indicate a lack of synchrony in ventricular depolarizations and contractions, which may be attributable to CHF or some other conduction abnormality. All but two of the responder patients had QRS complex widths greater than 150 msec, while all of the non-responder patients had QRS complex widths less than 150 msec. It appears that there is a trend showing that the patients with the worst conditions are more likely to benefit from pacing therapy.

A problem with the QRS width method of assessing "responsiveness" is that the margin of separation between those patients determined to be responders and non-responders is less than 10%. This narrow margin makes the method inaccurate. Therefore, a need exists for a patient identification method to separate the responders from the non-responders with a wide margin of separation. After considering the prior art relating to this invention, it can be seen that a need exists for an easy and accurate method and apparatus for determining whether a CHF patient is properly suited for pacing therapy. The present invention meets this need.

SUMMARY OF THE INVENTION

The present invention provides a method and apparatus for determining whether a patient with CHF will benefit from pacing therapy. The invention involves the steps of first measuring the patient's right and left ventricular pressures, and calculating a value based on the measured pressures. The next step is to determine whether the value indicates that the patient is a responder or a non-responder to pacing therapy by comparing the value to an empirically derived numeric threshold.

BRIEF DESCRIPTION OF THE DRAWINGS

The foregoing objects and advantages of the present invention will become apparent to those skilled in the art from the following detailed description of the preferred embodiments, especially when considered in conjunction with the accompanying drawings in which.

DETAILED DESCRIPTION OF THE PREFERRED EMBODIMENT

The present invention represents a method and apparatus for determining whether or not a CHF patient will benefit from cardiac pacing therapy using an implantable cardiac rhythm management device. As pointed out earlier, pacing therapy has been found to have both positive and negative acute impact on CHF patients, i.e. some CHF patients respond well to pacing therapy, and are referred to herein as "responders", while others are negatively effected, and are referred to as "non-responders". The embodiment detailed herein is intended to be taken as representative or exemplary of those methods and apparatuses that may be used to determine whether or not a patient will benefit from pacing therapy and is not intended to be limiting.

Figure 1:
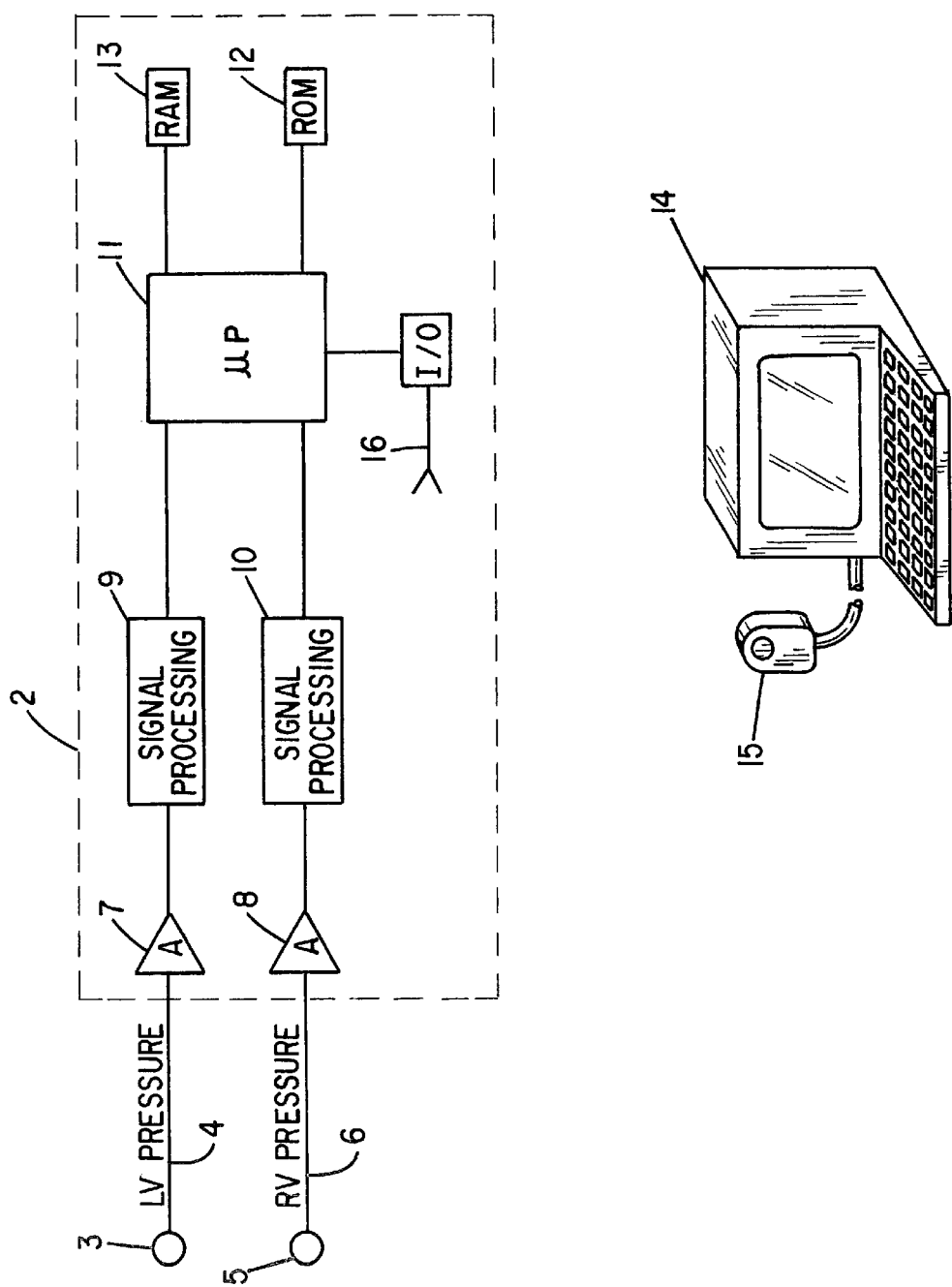
FIG. 1 is a hardware block diagram of one possible implementation of the inventive apparatus.

Referring first to FIG. 1, there is illustrated a hardware block diagram of one possible implementation of the inventive apparatus. The apparatus includes a first pressure sensor 3 that is disposed on a catheter or an electrical lead 4 with the pressure sensor positioned intracardiacally to detect the cyclic variations of left ventricular pressure. Typically, the pressure sensor is a solid-state pressure transducer capable of converting the pressure variations into electrical signals proportional thereto. Similarly, a second pressure sensor 5 on a catheter or a lead 6 is positioned intracardiacally to detect variations in right ventricular pressure. One example of a pressure sensor that may be used in this invention is a micromanometer.

The electrical signals from each of the transducers, or any pressure-sensing device that is used, are amplified by amplifiers 7 and 8 and signal processed by circuits 9 and 10 to remove noise artifacts therefrom. The signal processors 9 and 10 may include low-pass filtering circuits having an upper cutoff frequency of about 200 Hz.

The outputs from the signal processing circuits 9 and 10 are applied to a microprocessor 11 having an on-board A/D converter incorporated therein for converting the analog signals representative of the pressure versus time waveforms to digital quantities, as is well known in the art.

The microprocessor 11 includes a ROM memory 12 which is typically used to store a program of instructions and a RAM memory 13 for storing programmable quantities and computational operands.

Digital quantities may be transferred bi-directionally between the implanted device 2 and an external monitor 14 via a telemetry link, including a programmer wand 15, which when placed proximate an implanted antenna coil 16, permits RF pulses to be percutaneously delivered.

The parts shown in FIG. 1 may be externally located with respect to the body of the patient being tested. This apparatus may also be, for the most part, located inside of the patient's body. For example, the pressure-sensing devices, as described earlier, may be located in the ventricles of the heart. In addition, the circuitry of the apparatus may be located inside the patient's body. The broken line box 2 on FIG. 1 shows the circuitry that would be placed inside of the patent's body in a moisture impervious, hermetically sealed container, in much the same way that implantable cardiac rhythm management devices are presently packaged. The monitor would still be located outside of the patient's body, even if the rest of the apparatus was internal.

Figure 2:
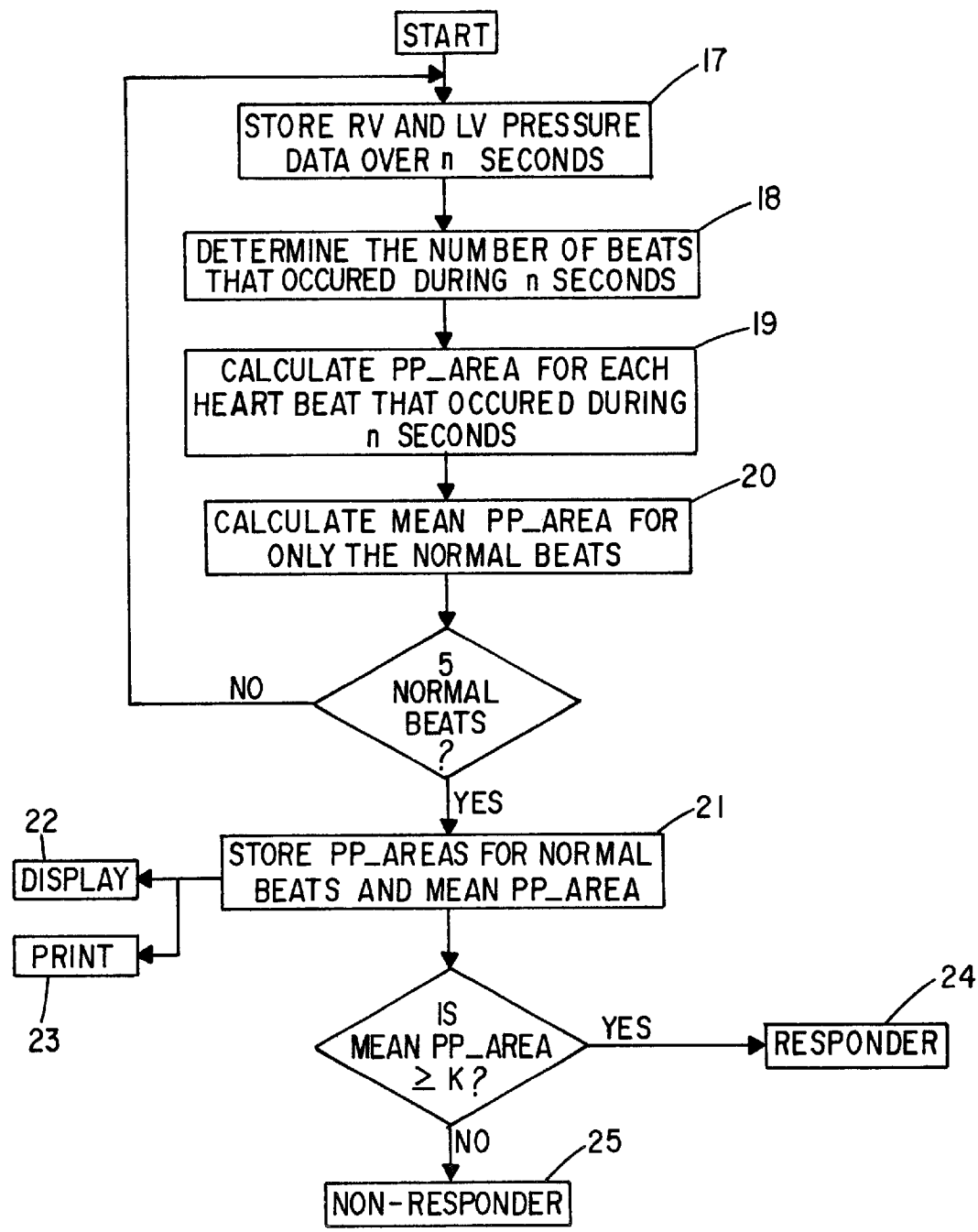
FIG. 2 is a software flow diagram useful in explaining the algorithm involved in the inventive method.

Referring now to the software flow diagram of FIG. 2, operation block 17 indicates that batches of data from the left ventricular pressure sensor and the right ventricular pressure sensor are stored over a pre-determined time period, n, which, for example, may be about 30 seconds. The batches of data are stored in the RAM memory 13 of the microprocessor 11 (from FIG. 1). In the preferred embodiment, the amount of time is thirty (30) seconds. It is to be understood that the thirty (30) second time period is arbitrary and a different amount of time can be used.

The next step in the method is to determine how many heart beats occurred during the predetermined time period. (FIG. 2, Block 18). In order to determine how many beats occurred during the predetermined time period, beat markers may be generated, which are used to indicate the start of a PP_Area calculation cycle.

One algorithm that is used, or could be used by a microprocessor or person, to generate beat markers calculates the LV pressure derivative, or slope, at all of the data points using the following formula:

$$f'x = \frac{f(x+2) + f(x+1) - f(x-1) - f(x-2)}{6}$$

The mean of all of the positive derivative points is then calculated. Next, for each normal beat, there is one and only one portion of the data whose derivatives are above the mean. The maximum derivative within that portion of data is then searched and used to indicate the start of a PP_Area calculation cycle, and is the beat marker. These marked data points have an array of times that correspond to them.

The reason that the data collected from the LV are used to determine the number of beats that occurred during the predetermined time period is because the LV is more stable than the RV.

Another way to generate beat markers is to use sensed events from the atrium (e.g. P-waves) or ventricle (e.g. R-waves). Another possibility would be to use R-waves from a surface ECG as beat markers.

The next step, as further illustrated by FIG. 2, is to calculate the PP_Area for each heartbeat, or cardiac cycle. (Block 19). The PP_Area is calculated on a beat-by-beat basis from the data collected PP_Area is defined as the area enclosed within the plot of RV pressure versus LV pressure during one entire cardiac cycle (the loop), divided by the area of the rectangle that surrounds the loop. The equation is:

$$PP\_Area_i = \frac{A1}{A2}$$

Figure 3:
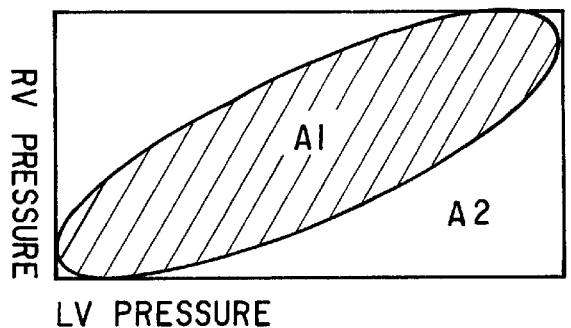
FIG. 3 is a graph of RV pressure shown in association with LV pressure, with the shaded loop denoted as A1 being the area of the LV-RV pressure loop and A2 being the area of the rectangle that encloses the LV-RV pressure loop.

FIG. 3 illustrates the quantities A1 and A2, which are part of the PP_Area algorithm. A1 is the shaded area inside the LV-RV elliptical pressure loop for beat i, and is defined as:

$$A1 = \frac{1}{2} \sum_{x=marker[i]}^{x<marker[i+1]} (RV_{x+1} + RV_x)(LV_x - LV_{x+1})$$

A2 is the area of the rectangle just large enough to enclose the pressure loop for beat i and is defined as:

$$A2 = (LV_{max} - LV_{min})(RV_{max} - RV_{min})$$

Therefore, the equation used to calculate PP_Area for beat i is:

$$PP\_Area_i = \frac{1}{2} \frac{\sum_{x=marker[i]}^{x<marker[i+1]} (RV_{x+1} + RV_x)(LV_x - LV_{x+1})}{(LV_{max} - LV_{min})(RV_{max} - RV_{min})}$$

The PP_Area is then calculated for each heart beat during the predetermined time period, or n seconds. The next step in the method is to take the mean of the PP_Areas for only the normal heart beats that occurred during the predetermined time period. (FIG. 2, Block 20). A normal heartbeat or normal cardiac cycle is one with normal intervals between two adjacent P waves or two adjacent R waves on an electrocardiogram, and that have good pressure waveforrm Normal cardiac cycles are also indicated by normal intervals between two adjacent beat markers.

In the preferred embodiment, if less than five (5) normal heart beats or cardiac cycles from any thirty (30) seconds of data are collected, then that thirty (30) seconds of data is disregarded, and another thirty (30) seconds of data is collected. This is repeated until five (5) PP_Areas are calculated from five (5) normal heartbeats occurring during a given thirty (30) second time period.

The PP_Areas from each of the normal heartbeats and the mean PP_Area for the patient may be stored as data in the memory of a microprocessor for later readout (Block 21). In addition, these data may be displayed in either graph form or table form (Block 22). The displays may also be printed. (Block 23).

The size of the loop that is shown in FIG. 3 varies depending upon the patient. A graph of RV pressure versus LV pressure from measurements taken from a patient with a healthy heart would be closer to a line (a small PP_Area). A patient with an asynchronous ventricular contraction has an oval RV-LV pressure loop (a large PP_Area). The more asynchronous the heart beat, the larger, or more round, the normalized RV-LV pressure loop and the larger the PP_Area value.

The next step, as shown in FIG. 2, is to determine whether the patient is a responder or non-responder. An empirically established, predetermined threshold, k, is used as a basis for comparison. A threshold value of 0.3 has been found to work well in the method to differentiate responders from non-responders. The threshold value of 0.3 has been empirically determined from data on a given sized patient sample. A PP_Area of greater than or equal to k, which is about 0.3, indicates a responder (Block 24), while a PP_Area of less than k indicates a non-responder (Block 25).

If the mean PP_Area is less than k, which is about 0.3, the patient is considered a non-responder, and pacing therapy is either not recommended or a different pacing therapy is suggested. The action recommended also may be to not pace at all or to pace at a long AV delay (e.g. 75% PR).

If the patient's PP_Area is greater than or equal to k, then the patient is considered a responder and pacing therapy is recommended. A site/AV delay optimization algorithm can then be performed on the responder to determine the optimum mode to be used in the particular patient's pacing therapy.

This method uses intrinsic data that is collected to determine whether a particular patient would benefit from pacing therapy. The invention is able to separate responders from non-responders with a wide margin, which increases the method's accuracy.

EXAMPLE

Patient tests have shown that the method/apparatus can be used to determine whether a patient will benefit from pacing therapy. The method results in a wide margin of separation between responders and non-responders. The method was tested on 29 CHF patients enrolled in the PATH-CHF study.

Figure 4:
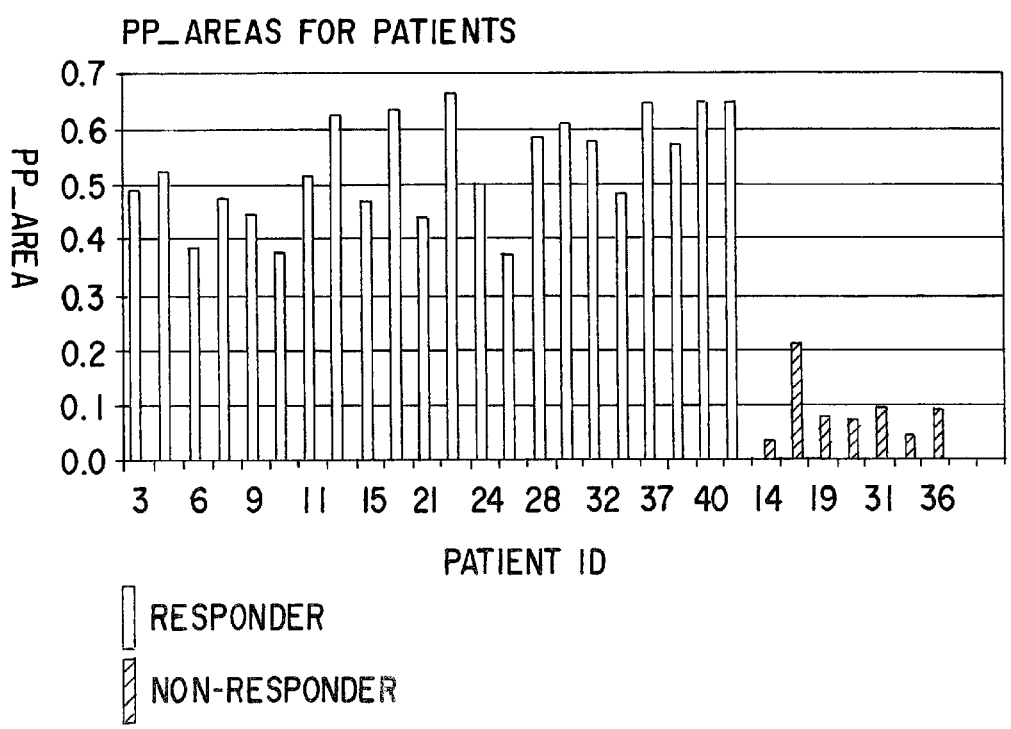
FIG. 4 is a graph of the mean intrinsic Normalized LV-RV pressure-loop areas (PP_Areas) for the 29 PATH-CHF patients.

The steps set forth in the flow chart in FIG. 2 were performed on the patients. The average intrinsic PP_Area values for each of the 29 patients were plotted and appear in FIG. 4. As can be seen, the PP-Area values of the responders are clearly separated from those of the non-responders.

The patients in the PATH-CHF study, besides being subjects of the testing of this method, were the patients used to determine the intrinsic values used in the method. In particular, they were used to determine the predetermined threshold, k, which was found to be about 0.3. The patients were acutely paced at right (RV), left (LV) and both ventricles (BV) with 5 AV delays. The AV delays were from 0 msec to intrinsic PR-30 msec at equal steps. Each combination of pacing mode and AV delay was randomly repeated five times on each patient in a five-beat pacing/fifteen-beat no-pacing duty cycle. Twenty-two (22) of the patients showed at least a 5% increase in LV pressure derivative maximum and/or pulse pressure, and were determined to be responders. The other seven (7) patients had less than a 5% increase in both LV pressure derivative maximum and pulse pressure and were determined to be non-responders.

The two sets of data collected for the two groups were separated. The mean values of the PP_Areas for each pacing chamber associated with each AV delay were plotted in two separate graphs. The graphs appear at FIGS. 5 and 6.

Figure 5:
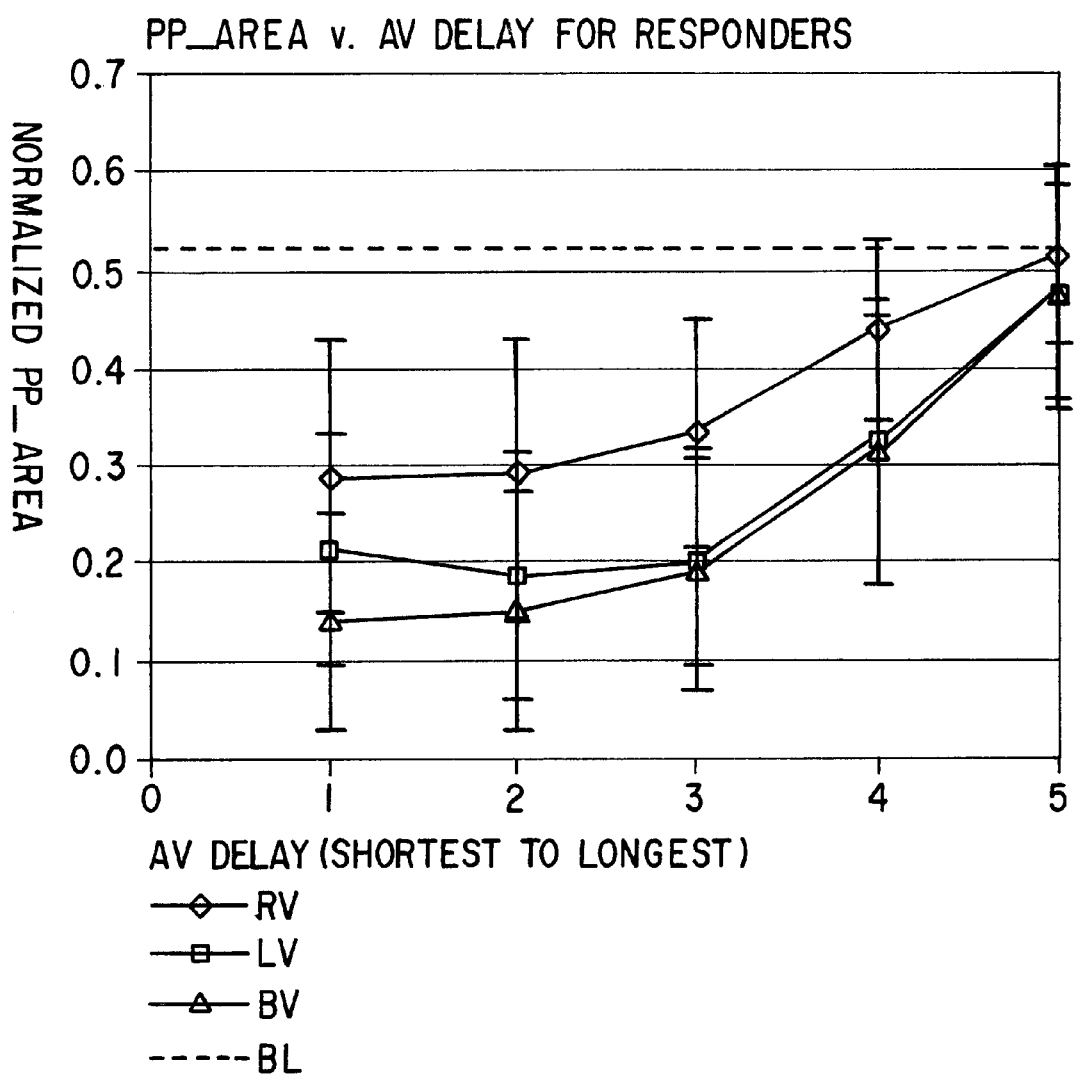
FIG. 5 is a graph of the mean paced PP_Areas of responders during pacing at three (3) pacing modes and five (5) Atrioventricular (AV) Delays.

FIG. 5 shows the mean values of the PP_Areas recorded for the responders during the paced beats. The intrinsic baseline, which is represented by the dotted line, is the mean value of all of the responders' PP_Areas for the non-paced beats. The baseline for the responders was 0.53±0.09.

Figure 6:
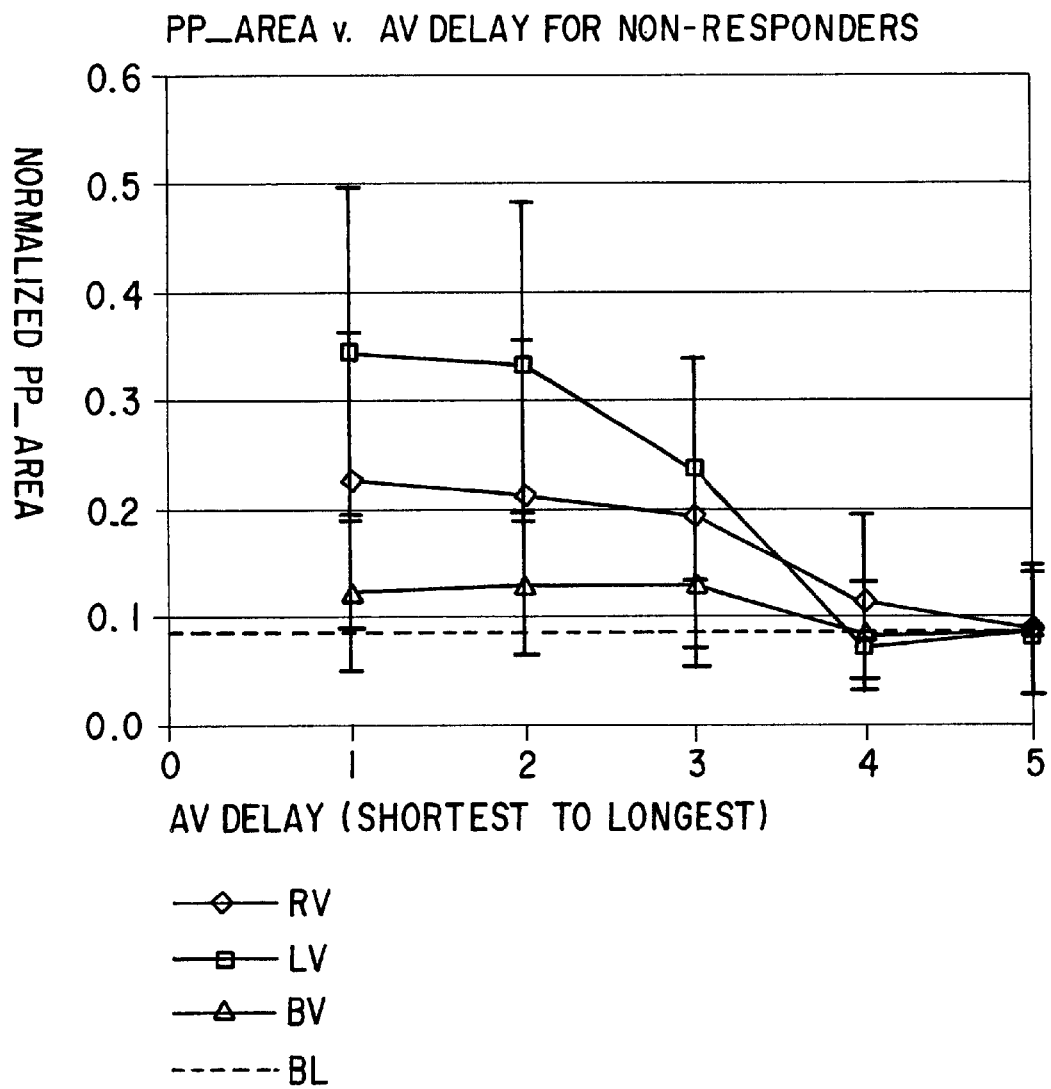
FIG. 6 is a graph of the mean paced PP_Areas of non-responders shown in association with three (3) pacing modes and five (5) AV Delays.

FIG. 6 shows the mean values of the PP_Areas recorded for the non-responders during the paced beats. Again, the intrinsic baseline for the non-responders is represented by a dotted line and is the mean value of all of the non-responders' PP_Areas for the non-paced beats. The baseline for the non-responders is 0.09±0.05.

The differences in the intrinsic baseline values between responders and non-responders were statistically significant (p<0.001). As can be seen by looking at FIGS. 5 and 6, the PP_Area vs. AV Delay curves are opposite for responders and non-responders.

The intrinsic value of about 0.3 for the predetermined threshold, k, is used in the method to differentiate between responders and non-responders because it is the midway point between the two intrinsic baseline values of the PP_Areas for the responders and non-responders. For example, the midway point between 0.09 and 0.53 is approximately 0.3. Using the threshold of 0.3 in the method results in a separation margin of over 30%. This separation margin is much larger than the 10% separation margin in the QRS complex width method. Therefore, this method is a superior and more accurate method.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedure, can be accomplished without departing from the scope of the invention itself. Hence, the scope of the invention is to be determined from the appended claims.

What is claimed is:

1. A method for determining whether a patient with congestive heart failure (CHF) will benefit from pacing therapy, said method comprising the steps of:
   (a) measuring right ventricular (RV) and left ventricular (LV) pressures;
   (b) calculating a value based on the RV and LV pressures; and
   (c) determining whether the patient is a responder or a non-responder to pacing therapy based on the value.

2. The method as defined in claim 1 wherein calculating the value includes calculating PP_Area, and wherein determining whether the patient is a responder or a non-responder to pacing therapy includes comparing the PP_Area to a predetermined threshold.

3. The method as defined in claim 2 wherein the predetermined threshold is about 0.3, with the PP_Area being greater than or equal to about 0.3 indicating that the patient is a responder, and with the PP_Area being less than about 0.3 indicating that the patient is a non-responder.

4. The method as defined in claim 2 wherein the step of measuring the RV and LV pressures is performed over a predetermined time period, and wherein the step of calculating PP_Area is conducted for each heart beat occurring during the predetermined time period, and further comprising the step of calculating a mean PP_Area of the PP_Areas only from normal heart beats during the predetermined time period, said mean PP_Area being used in determining whether the patient is a responder or non-responder to pacing therapy by comparing the mean PP_Area to said predetermined threshold.

5. The method as defined in claim 4 wherein the predetermined threshold is about 0.3, with the mean PP_Area being greater than or equal to about 0.3 indicating that the patient is a responder, and with the mean PP_Area being less than about 0.3 indicating that the patient is a non-responder.

6. The method as defined in claim 4 wherein the predetermined time period is about thirty (30) seconds.

7. The method as defined in claim 6 wherein said predetermined threshold is about 0.3, with the mean PP_Area being greater than or equal to about 0.3 indicating that the patient is a responder, and with the mean PP_Area being less than about 0.3 indicating that the patient is a non-responder.

8. The method as defined in claim 6 wherein after the step of calculating the PP_Area for each heart beat occurring during the thirty second time period, a further step of determining whether at least five (5) PP_Areas have been calculated from data collected during a given thirty (30) second time period, and if so, proceeding with the further steps of calculating the mean of at least five PP_Areas, comparing the mean PP_Area to the predetermined threshold, and determining whether the patient is a responder or a non-responder, and if at least five (5) PP_Areas have not been calculated, then further comprising a step of disregarding earlier collected data and repeating the step of calculating the PP_Area for each heart beat during a next thirty (30) second time period until at least five (5) PP_Areas are calculated from five (5) normal heart beats occurring during a next thirty (30) second time period.

9. The method as defined in claim 8 wherein said predetermined threshold is about 0.3, with the mean PP_Area being greater than or equal to about 0.3 indicating that the patient is a responder, and with the mean PP_Area being less than about 0.3 indicating that the patient is a non-responder.

10. The method as defined in claim 4 and further comprising the step of storing the PP_Area of each normal heart beat and the mean PP_Area as data in a memory for later readout.

11. The method as defined in claim 10 and further comprising the step of displaying the data in graph form.

12. The method as defined in claim 10 and further comprising the step of displaying the data in table form.

13. An apparatus for determining whether a patient with CHF will benefit from pacing therapy comprising:
   (a) means for sensing pressure variations in the left and right ventricle of patient's heart and producing an electrical signal proportional thereto;
   (b) means for converting the electrical signal to a digital quantity;
   (c) a microprocessor having a memory for storing samples of the digital quantities over a predetermined time period;
   (d) means for determining how many heart beats occur during the predetermined time period;
   (e) means for determining whether a heart beat is normal or not;
   (f) means for calculating PP_Areas for heart beats occurring during the predetermined time period, and a mean value of the PP_Areas;
   (g) means for determining whether the mean PP_Area of a given pacing therapy is above or below a predetermined threshold, as an indicator of whether the patient is a responder or a non-responder to the given pacing therapy.

14. The apparatus as defined in claim 13 wherein the means for sensing pressure variations is an external device.

15. The apparatus as defined in claim 13 wherein the means for sensing pressure variations is an internal device.

16. The apparatus as defined in claim 13 wherein the means for sensing pressure variations is a micromanometer.

17. An apparatus for determining whether a patient with CHF will benefit from pacing therapy, comprising:
   (a) an implantable electronics module containing a microprocessor and a memory coupled to the microprocessor for storing a program of instructions and calculated operands;
   (b) pressure transducers positioned to sense left and right ventricular pressures and for producing electrical signals proportional thereto;
   (c) means for applying the electrical signals as digital quantities to the microprocessor;
   (d) means responsive to the execution of the program for computing a mean value of pulse pressure areas from the digital quantities over a predetermined time interval; and
   (e) means including the microprocessor for determining whether the computed mean value is greater than, equal to or less than a predetermined threshold as an indicator of whether the patient will benefit from pacing therapy.

* * * * *